United States Patent
Ni et al.

(10) Patent No.: US 12,214,256 B2
(45) Date of Patent: Feb. 4, 2025

(54) DEVICE FOR EFFICIENTLY EXTRACTING ADAPTIVELY SELECTED CONTACTLESS MULTI-PLAYER HEART RATES

(71) Applicant: TIANJIN UNIVERSITY, Tianjin (CN)

(72) Inventors: Guangjian Ni, Tianjin (CN); Wei Kang, Tianjin (CN); Zihao Xu, Tianjin (CN)

(73) Assignee: TIANJIN UNIVERSITY, Tianjin (CN)

( * ) Notice: Subject to any disclaimer, the term of this patent is extended or adjusted under 35 U.S.C. 154(b) by 263 days.

(21) Appl. No.: 17/849,175

(22) Filed: Jun. 24, 2022

(65) Prior Publication Data
US 2023/0063940 A1    Mar. 2, 2023

(30) Foreign Application Priority Data
Sep. 2, 2021 (CN) .......................... 202111024375.8

(51) Int. Cl.
| | | |
|---|---|---|
| A63B 24/00 | (2006.01) | |
| A63B 71/06 | (2006.01) | |
| A63B 102/18 | (2015.01) | |
| A63B 102/24 | (2015.01) | |

(52) U.S. Cl.
CPC ...... *A63B 24/0062* (2013.01); *A63B 71/0622* (2013.01); *A63B 2024/0034* (2013.01); *A63B 2102/18* (2015.10); *A63B 2102/24* (2015.10); *A63B 2220/05* (2013.01); *A63B 2220/806* (2013.01); *A63B 2230/06* (2013.01); *A63B 2243/0025* (2013.01); *A63B 2243/0037* (2013.01); *A63B 2243/0066* (2013.01); *A63B 2243/0095* (2013.01)

(58) Field of Classification Search
CPC ............ A63B 24/0062; A63B 71/0622; A63B 2102/18; A63B 2102/24; A63B 2024/0034; A63B 2220/05; A63B 2220/806; A63B 2230/06; A63B 2243/0025; A63B 2243/0037; A63B 2243/0066; A63B 2243/0095
See application file for complete search history.

(56) References Cited

U.S. PATENT DOCUMENTS

| | | | | |
|---|---|---|---|---|
| 2011/0251493 | A1* | 10/2011 | Poh | ...................... G06F 18/2134 382/128 |
| 2013/0130845 | A1* | 5/2013 | Marty | ..................... G06V 40/23 473/459 |
| 2014/0067098 | A1* | 3/2014 | Regan | ....................... G06T 7/20 700/91 |

(Continued)

*Primary Examiner* — Malina D. Blaise

(57) ABSTRACT

The present disclosure discloses a device for efficiently extracting adaptively selected contactless multi-player heart rates includes: an acquisition module that covers a court to obtain videos from a plurality of angles during players training; a valid player obtaining module configured to remove players with low contributions to training and games in the videos; a facial ROI extraction module configured to detect whether the facial ROIs of valid players contain perfect eye region features, and use the facial ROIs containing the eye region features as best facial ROIs for heart rate extraction; and an analysis and estimation module configured to analyze the detected best facial ROIs by using blind source separation, and estimate a RGB signal by a JADE algorithm to obtain the heart rate values of the valid players.

5 Claims, 3 Drawing Sheets

(56) References Cited

U.S. PATENT DOCUMENTS

| | | | |
|---|---|---|---|
| 2014/0114165 A1* | 4/2014 | Walker | A61B 3/113 |
| | | | 600/383 |
| 2014/0180451 A1* | 6/2014 | Marty | G06V 40/23 |
| | | | 700/91 |
| 2015/0302158 A1* | 10/2015 | Morris | G06V 10/25 |
| | | | 702/19 |
| 2019/0287682 A1* | 9/2019 | van Zon | G16H 50/30 |
| 2020/0008023 A1* | 1/2020 | Tran | A42B 3/0433 |
| 2020/0085312 A1* | 3/2020 | Tzvieli | A61B 5/02055 |
| 2020/0155944 A1* | 5/2020 | Witchey | H04L 9/3239 |
| 2021/0275034 A1* | 9/2021 | Frank | G01J 5/0265 |

* cited by examiner

DEVICE FOR EFFICIENTLY EXTRACTING ADAPTIVELY SELECTED CONTACTLESS MULTI-PLAYER HEART RATES

CROSS-REFERENCE TO RELATED APPLICATION

This application claims priority from the Chinese patent application 2021110243758 filed Sep. 2, 2021, the content of which is incorporated herein in the entirety by reference.

FIELD OF THE APPLICATION

The present disclosure relates to the field of image data processing/analysis, in particular to a device for efficiently extracting adaptively selected contactless multi-player heart rates.

BACKGROUND ART

Actual combat training is required in a multi-player ball game. During the actual combat training, it is required for coaches to know athletic states of players on a court timely, and the athletic states are usually related to physiological status of the players on the court during actual movement, therefore, real-time understanding of heart rates and other physiological indicators of the players on the training ground helps the coaches grasp the actual states of the players during training, thereby facilitating rehabilitation training and technical and tactical guidance after the game. Currently, the heart rates and other physiological indicators are usually acquired by a wearable device. However, for group ball games, the players may not wear one-piece sportswear, so the wearable device may not be installed properly during the sports, and extra burden is also increased for the players, which has a certain impact on a competitive state. Therefore, it is necessary to adopt a contactless method to measure the heart rate in real time. At present, the contactless real-time heart rate measurement method mainly aims to extract the heart rate values by analyzing the RGB face images.

In a multi-player ball game scenario, such as volleyball training, 6 players are provided by both sides on the training ground respectively, a total of 12 players. The existing method for extracting the heart rate values based on the RGB face images analysis has the following problems:

(1) At present, a DV method is usually used for on-site training video recording, which would lead to uneven video acquisition direction, and could not acquire live videos stably from multiple angles simultaneously, resulting in missing faces from certain angles, and thus could not accurately detect the heart rates of the players at that moment;

(2) In the same video analysis period, there are too many players on the screen, and the calculation load would increase when extracting the heart rate of multiple players at the same time. Therefore, it is urgent to realize the method of efficiently analyzing and calculating the video and extracting the heart rates with high accuracy;

(3) When extracting the heart rates of multiple players, it is necessary to detect facial regions of interest (ROI) of the players to complete the heart rate extraction. However, due to the problem of the video acquisition angle, the full-frontal face information could not be obtained well, so the heart rate extraction could not be accurately realized.

BRIEF SUMMARY OF THE DISCLOSURE

The present disclosure provides a device for efficiently extracting adaptively selected contactless multi-player heart rates. The device realizes the efficient extraction of the heart rates of the players by acquiring RGB images of multiple ball players on a training ground according to a denoising algorithm and adaptive selection provided by the present disclosure. The present disclosure could adaptively, quickly and accurately extract the effective heart rate values of the players from a multi-player ball training video, as described below in details:

In a first aspect, a device for efficiently extracting adaptively selected contactless multi-player heart rates includes:
  an acquisition module that covers a court to obtain videos from a plurality of angles during players training;
  a valid player obtaining module configured to remove players with low contributions to training and games in the videos;
  a facial region of interest (ROI) extraction module configured to detect whether the facial ROIs of valid players contain perfect eye region features, and use the facial ROIs containing the eye region features as best facial ROIs for heart rate extraction;
  and
  an analysis and estimation module configured to analyze the detected best facial ROIs by using blind source separation, and estimate a RGB signal by a JADE algorithm to obtain the heart rate values of the valid players.

In a second aspect, a device for efficiently extracting adaptively selected contactless multi-player heart rates is applied to volleyball, basketball, soccer, rugby, baseball, and ice hockey.

In a third aspect, a device for efficiently extracting adaptively selected contactless multi-player heart rates is provided, includes:
  a processor and a memory, wherein program instructions are stored in the memory, and the processor calls the program instructions stored in the memory to cause the device to perform the following steps:
  obtaining videos from a plurality of angles during players training, wherein the scope of the videos covers a court;
  removing players with low contributions to training and games in the videos to obtain valid players;
  detecting whether facial ROIs of the valid players contain perfect eye region features, and using the facial ROIs containing the eye region features as best facial ROIs for heart rate extraction; and
  analyzing the detected best facial ROIs by using blind source separation, and estimating a RGB signal by a JADE algorithm to obtain the heart rate values of the valid players.

In a fourth aspect, a computer readable storage medium is provided, wherein the computer readable storage medium stores a computer program, and the computer program includes program instructions that cause the processor to perform the device steps in the third aspect when the program instructions are executed by the processor.

The technical solution provided by the present disclosure has the beneficial effects that:

(1) In order to solve the problem of traditional video acquisition by DV, cameras are deployed in the plurality of angles to obtain videos from all angles of the court, instead of a single DV shooting, which is convenient for subsequent automatic selection of the best angle videos for heart rate extraction and analysis. For example: 8-channel cameras cover all angles of the court, in order to obtain stable and multi-directional training videos; meantime, ordinary RGB video images obtained are used instead of wearable devices to acquire and extract the heart rates of the players, and contactless video acquisition protects the wearable devices from an unnecessary impact on the competitive state of the players;

(2) After obtaining the multi-angle videos, heart rate extraction and calculation is required, but the redundancy of invalid information in the videos greatly reduces the calculation efficiency. For this purpose, the present disclosure proposes an idea of "denoising" the videos before heart rate extraction to remove the invalid players in video clips used for heart rate extraction, and to improve the calculation speed of subsequent simultaneous heart rate extraction for multiple people;

(3) After obtaining the video clips with valid player information, the faces of the valid players in the videos are detected to obtain the facial ROIs. However, due to the problem of the video acquisition angle, the frontal face information may not be obtained. For this purpose, the present disclosure proposes an adaptive detection to obtain the ROI information on the front of the face, that is, detecting whether the facial ROIs contain perfect eye area features, i.e., detecting whether binocular eyeballs with closed contour are contained, and calculating the average value of the sum of roundness of the eyeballs, to further ensure that the selected facial ROIs are the frontal position of the face; when the ROIs are found not to include the perfect eye region features, the detected face is considered incomplete, and the videos obtained from other camera angles at the same time period are required to be detected to obtain the facial ROIs, until the best facial ROIs position containing the perfect eye region features and the maximum average value of the sum of roundness of the eyeballs are obtained for heart rate extraction;

(4) The Blind Source Separation (BSS) is used to analyze the detected best facial ROIs, and the RGB signal in the facial ROIs is estimated by the JADE algorithm to obtain the heart rate values of the players;

(5) By "denoising" the obtained multi-angle player videos, valid player information is obtained, and the automatic selection method of the facial ROIs is comprehensively used, which improves the calculation efficiency while ensuring the accuracy of heart rate extraction, provides a technical support for replay of relevant training and games in the ball game scenario, effectively improves the daily training effect of ball games in China, and achieves good results in the games. The solution could be applied to volleyball, basketball, football, and other application scenarios, and is expected to obtain good feedback and social benefits.

DETAILED DESCRIPTION OF THE PRESENT DISCLOSURE

In order to make objects, technical solutions and advantages of the present application clearer, detailed description is further made below to the embodiments of the present disclosure.

Embodiment 1

Figure 1:
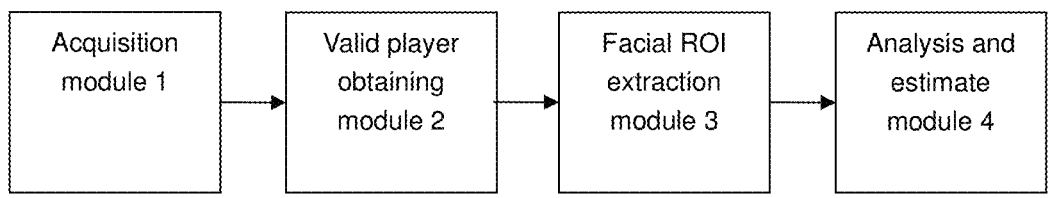
FIG. 1 is a schematic diagram illustrating a structure of a device for efficiently extracting adaptively selected contactless multi-player heart rates.

A device for efficiently extracting adaptively selected contactless multi-player heart rates, as shown in FIG. 1, wherein the device includes:
an acquisition module 1 that covers a court to obtain videos from a plurality of angles during players training;
a valid player obtaining module 2 configured to remove players with low contributions to training and games in the videos;
a facial region of interest (ROI) extraction module 3 configured to detect whether the facial ROIs of valid players contain perfect eye region features, and use the facial ROIs containing the eye region features as best facial ROIs for heart rate extraction; and
an analysis and estimation module 4 configured to analyze the detected best facial ROIs by using blind source separation, and estimate a RGB signal by a JADE algorithm to obtain the heart rate values of the valid players.

Figure 2:
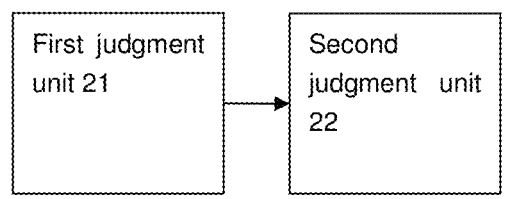
FIG. 2 is a schematic diagram illustrating a structure of a valid player obtaining module.

Referring to FIG. 2, the valid player obtaining module 2 includes:
a first judgment unit 21 configured to judge whether a movement trajectory of a ball is consistent with a movement direction of an observed player; and
a second judging unit 22 configured to judge whether the movement trajectory of the ball is consistent with a movement change rate of the observed player;

If the two judgments are consistent, that is, when both the movement direction and the movement change rate are consistent, the player is regarded as a valid player, otherwise the player is removed from the current video.

Further, the first judgment unit 21 in FIG. 2 includes:
a first marking subunit configured to mark the movement trajectory of the ball in a video clip to obtain a ball position coordinate set;
a second marking subunit configured to mark the trajectory position of the player appearing in the video clip to obtain a player position coordinate set; and
a first calculation and judgment subunit configured to calculate values of the average change angles of the ball position coordinate set and the player position coordinate set respectively by using the obtained the ball position coordinate set and the player position coordinate set. If the average change angles of the ball position coordinate set and the player position coordinate set are less than a first threshold, the change directions of the two are considered to be consistent.

Herein, the above first threshold is set according to needs in practical application, and is not limited in the embodiments of the present disclosure.

In an embodiment, the second judgment unit 22 in FIG. 2 includes:

a second calculation and judgment subunit configured to calculate average values of position change rates of the movement trajectory of the ball and the trajectory position of the observed player, if the average position change rate is less than a second threshold, the position change rates of the movement trajectory of the ball and the trajectory position of the observed player are considered to be consistent.

That is, the embodiments of the present disclosure propose an idea of "denoising" the videos before heart rate extraction through the two judgments to remove invalid players in the video clips used for heart rate extraction, and to improve the calculation speed of subsequent simultaneous heart rate extraction for multiple people.

Figure 3:
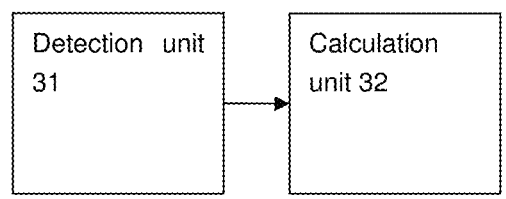
FIG. 3 is a schematic diagram illustrating a structure of a facial region of interest (ROI) extraction module.
Figure 4:
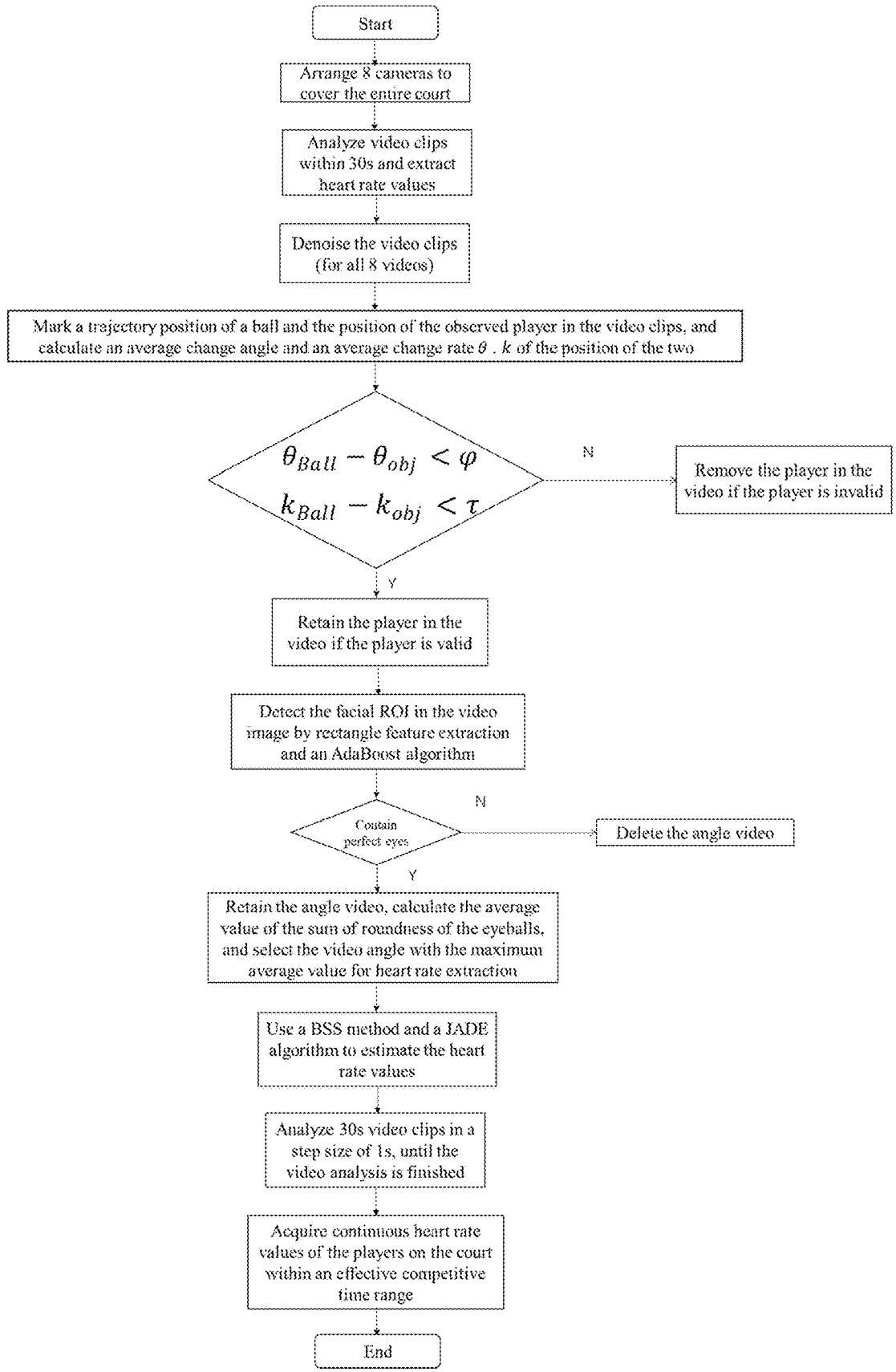
FIG. 4 is a flow chart of a device for efficiently extracting adaptively selected contactless multi-player heart rates.
Figure 5:
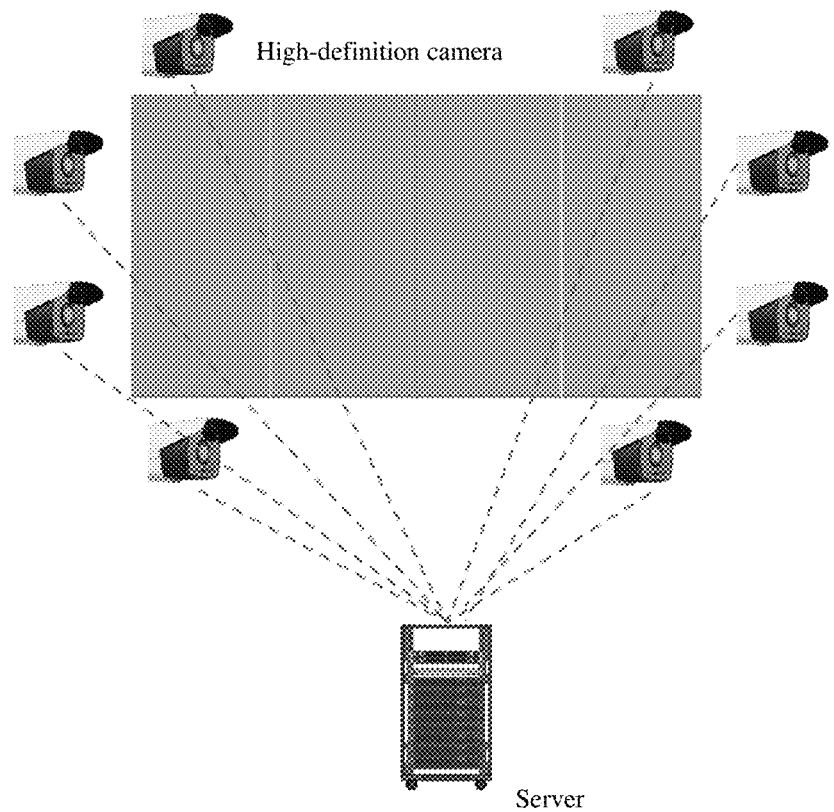
FIG. 5 is a schematic diagram of video acquisition and analysis.

As shown in FIG. 3, the facial ROI extraction module 3 further includes:

a detection unit 31 configured to detect whether the facial ROIs of the valid players contain binocular eyeballs with closed contour;

a calculation unit 32 configured to calculate the average value of the sum of roundness of the eyeballs when the binocular eyeballs with closed contour are contained; and when detecting a plurality of video angles that contain the perfect eye features, calculate the average value of the sum of roundness of a plurality of eyeballs in each ROI and select the angle video corresponding to the maximum average value as the best angle video.

In the specific implementation, when the facial ROIs of the valid players do not contain binocular eyeballs with closed contour, the video from the current angle is considered invalid, and videos continue to be selected from other angles until all ROIs are retrieved to see whether they contain the perfect eye region features, which ensures that all ROIs are traversed and improves the detection accuracy.

In an embodiment, the above multi-angle video acquired by the acquisition module 1 could be used for replay after training and games, and the specific use and replay steps are no more detailed descript in the embodiments of the present disclosure.

Consequently, the embodiments of the present disclosure realize the adaptive, fast and accurate extraction of the effective heart rate values of the players from the multi-player ball training video through the mutual cooperation of the above components, which has high accuracy and satisfies various needs in practical application.

Embodiment 2

Further description is made below to the Embodiment 1 by taking a multi-player volleyball training as an example in combination with specific examples, calculation formulas, and FIGS. 1-5, as described below in details:

The solution is specifically as follows: multi-channel cameras are deployed on a volleyball court, for example: a 8-channel camera is used to cover the entire volleyball court to obtain videos from a plurality of angles during volleyball players training, and the subsequent steps include extracting facial ROIs of the players through the acquired multi-angle videos, analyzing RGB images in the facial ROIs, and then extracting physiological indicators of the players such as heart rates during the actual combat training.

The embodiments of the present disclosure use cameras as the acquisition module for discussion, and the number of cameras is not limited. During the specific implementation, the selection of components and the setting of the number could be performed according to the needs in practical application, and the embodiments of the present disclosure make no limitation to this.

Taking the volleyball training as an example, 6 players were provided by both sides on the court respectively, a total of 12 players. When the heart rate extraction was performed, a continuous video clip was actually analyzed, and the continuous heart rate values of 12 players were obtained respectively. In the embodiments of the present disclosure, 30 s was used as a time window for video analysis, and continuous heart rate extraction was performed in an increment of 1 s. Therefore, taking how to process the video within 30 s as an example, the rapid extraction of the effective heart rate values of 12 players was investigated.

The above time window value and the increment value are all set according to the needs in practical application, and are not limited in the embodiments of the present disclosure.

1) After recording the multi-angle video during training, video analysis and heart rate extraction are performed.

Wherein when performing heart rate extraction analysis, a large number of video analysis calculations were performed, and a lot of invalid information appeared in the analyses. For example, some players have no actual actions on the court or do not contribute to the team during this period. The invalid information had a great impact on the analysis efficiency, and the results were meaningless. Therefore, the acquired video clip should be denoised first, and the players who do not need attention in the video clip are removed, thereby focusing on effectively analyzing the heart rate indicators of relevant athletes.

2) Removal of irrelevant players in the video clip can be measured by the contribution to training and games by the players, that is, measured by the players' attention to the ball. Players with low attention to the ball are removed from the video clip to reduce the amount of calculation for subsequent heart rate extraction. The specific methods are as follows:

First, a movement trajectory of the ball in the video clip was marked to obtain the ball position coordinate set (X, Y)$_{Ball}$ and then, a trajectory position of the player appearing in the video clip was marked to obtain the player position coordinate set (X, Y)$_{obj}$. The values of the average change angles $$\theta = \arctan\left(\frac{|y_2 - y_1|}{|x_2 - x_1|}\right)$$

of the movement trajectory of the ball and the position coordinate set of the observed player were calculated respectively, If the average change angle was $|\theta_{Ball} - \theta_{Obj}| < \varphi$ ($\varphi$ value may be adjusted according to the needs, and default $\varphi$ value was 0.5° according to the actual measurement of volleyball training), the change directions of the movement trajectory of the ball and the position coordinate set of the observed player were considered to be consistent approximately.

Further, the average values of position change rates $$k = \frac{|y_2 - y_1|}{|x_2 - x_1|}$$

of the movement trajectory of the ball and the trajectory position of the observed player are calculated, respectively. If the average position change rate was $|k_{Ball} - k_{Obj}| < \tau$ ($\tau$ value may be adjusted according to the needs, and default $\tau$ is 0.5° according to the actual measurement of volleyball training), the position change rates of the movement trajectory of the ball and the trajectory position of the observed player are considered to be consistent approximately.

When the movement trajectory of the ball is consistent with the movement direction and movement change rate of the observed player, the player is considered to be related to the movement trajectory of the ball, and the player is retained in the video as a valid player, otherwise the player is removed from the video. Through the above two judgments, the valid players in the video were screened, and the valid players would be further analyzed in the follow-up to obtain the heart rate values.

3) After obtaining the valid players in the video, face detection of a plurality of valid players is performed at the same time to obtain the facial ROIs of the plurality of valid players;

In the specific implementation, rectangle feature extraction and an AdaBoost algorithm could be used to detect the facial ROI in the video image. In order to better extract the heart rates of the valid players in the follow-up, the ROI of the full-frontal face is obtained as much as possible. However, due to the problem of the video acquisition angle, the ROI of the full-frontal face may not be obtained necessarily, so adaptive verification is required.

The specific operations include:
verifying whether each ROI contains the perfect eye region features (namely, the binocular eyeballs with closed contour are contained), if not, considering that the video in this angle is invalid, and continuing to select the video from other angles until all ROIs are retrieved to see whether they contain the perfect eye region features; and calculating the average value of the sum of roundness of a plurality of eyeballs in each ROI and selecting the angle video corresponding to the maximum average value as the best angle video for the heart rate extraction, when detecting a plurality of video angles that contain the perfect eye features.

4) After obtaining the videos of the valid players in the best facial ROIs that contain the perfect eye region features and the maximum average value of roundness of the eyeballs, the blind source separation (BSS) method is used to extract the heart rates, and the JADE algorithm could be used to estimate the heart rates from the RGB images of the best facial ROIs.

In the specific implementation, the continuous heart rate values of the players on the court within an effective competitive time range are extracted in an increment of 1 s. The above BSS method and the JADE algorithm are all well-known algorithms in the art, and will not detailed described in the embodiments of the present disclosure.

The embodiments of the present disclosure could be applied to volleyball training and competition scenarios. 8 cameras are arranged around the standard volleyball court, covering the entire volleyball court, and training and game videos could be obtained from all angles, so as to obtain the frontal face video information of the players.

5) The acquired multi-angle videos could be used for replay after training and games.

When replaying the game, the acquired videos were analyzed and processed through the following steps to obtain the continuous heart rate values of the players on the court within the effective competitive time range.

(1) The acquired multi-angle videos were preliminarily analyzed. The method was used to "denoise" the video and remove the player information in the videos that did not contribute to the movement, so as to reduce the amount of calculation for the subsequent heart rate extraction;

(2) After acquiring the videos with the valid players, the video angles were screened, and meantime, the method was used to screen the video angles to obtain the best facial ROIs for subsequent heart rate extraction and calculation;

(3) After obtaining the best facial ROI videos, the BSS method was used to extract the heart rates to obtain the effective heart rate values which were used for replay analysis and guidance of the athletic states and performance of the players on the court after the training and games.

Consequently, the embodiments of the present disclosure realize the adaptive, fast and accurate extraction of the effective heart rate values of the players from the multi-player ball training video through the mutual cooperation of the above components, which has high accuracy and satisfies various needs in practical application.

Embodiment 3

Figure 6:
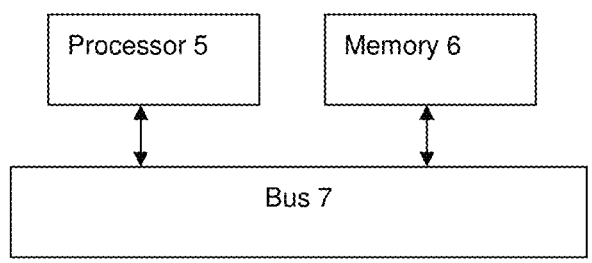
FIG. 6 is another schematic diagram illustrating a structure of a device for efficiently extracting adaptively selected contactless multi-player heart rates.

As shown in FIG. 6, a device for efficiently extracting adaptively selected contactless multi-player heart rates is provided, includes:
a processor 5 and a memory 6, wherein program instructions are stored in the memory 6, and the processor 5 calls the program instructions stored in the memory 6 to cause the device to perform the following steps:
obtaining videos from a plurality of angles during players training, wherein the scope of the videos covers a court; removing players with low contributions to training and games in the videos to obtain valid players;
detecting whether facial ROIs of the valid players contain perfect eye region features, and using the best facial ROIs containing the eye region features for heart rate extraction; and
analyzing the detected best facial ROIs by using blind source separation, and estimating a RGB signal by a JADE algorithm to obtain the heart rate values of the valid players.

Wherein the step of removing players with low contributions to training and games in the videos to obtain valid players specifically includes:
judging whether a movement trajectory of the ball is consistent with a movement direction of the observed player; and judging whether the movement trajectory of the ball is consistent with a movement change rate of the observed player;

If the two judgments are consistent, the player is a valid player, otherwise the player is removed from the current video.

In an embodiment, the step of judging whether the movement trajectory of the ball is consistent with the movement direction of the observed player specifically includes:
marking the movement trajectory of the ball in the video clip to obtain a ball position coordinate set; and marking the trajectory position of the player appearing in the video clip to obtain a player position coordinate set; and
calculating the average values of the change direction angles of the ball position coordinate set and the player position coordinate set respectively. If the average change angle of the two is less than a first threshold, the change directions of the two are considered to be consistent.

In an embodiment, the step of judging whether the movement trajectory of the ball is consistent with the movement change rate of the observed player specifically includes: calculating the average values of position change rates of the movement trajectory of the ball and the trajectory position of the observed player, if the average change rate is less than a second threshold, the change rates of the two are considered to be consistent.

Wherein the step of detecting whether facial ROIs of the valid players contain perfect eye region features, and using the best facial ROIs containing the eye region features for heart rate extraction specifically includes:
  detecting whether the facial ROIs of the valid players contain binocular eyeballs with closed contour; and
  calculating the average value of the sum of roundness of the eyeballs when the binocular eyeballs with closed contour are contained; and calculating the average value of the sum of roundness of a plurality of eyeballs in each ROI and select the angle video corresponding to the maximum average value as the best angle video, when detecting a plurality of video angles that contain the perfect eye features.

It should be noted that, the device description in the above embodiments corresponds to the method description in the embodiments, and no more detailed description will be made in the embodiments of the present disclosure.

The executive body of the processor 5 and the memory 6 could be a computer, a single chip computer, a microcontroller, and other devices having a calculation function. When the specific implementation, the embodiments of the present disclosure make no limitation, and selection is performed according to the needs in practical application.

Data signals are transmitted between the memory 6 and the processor 5 by a bus 7, and no more detailed description will be made in the embodiments of the present disclosure.

Embodiment 4

Based on the same inventive concept, the embodiments of the present disclosure further provide a computer readable storage medium which includes stored programs and controls the device where the storage medium is located to perform the steps in the Embodiments 1-3 when the program runs.

The computer readable storage medium includes but is not limited to a flash memory, a hard disk, a solid state disk, etc.

It should be noted that, the readable storage medium in the above embodiments corresponds to the method in the embodiments, and no more detailed description will be made in the embodiments of the present disclosure.

The embodiments may be implemented, in whole or in part, by software, hardware, firmware or any combination thereof. When implemented by the software, the embodiments could be implemented, in whole or in part, in the form of a computer program product. The computer program product includes one or more computer instructions. When the computer program instructions are loaded and executed on a computer, the procedures or functions according to the embodiments of the present disclosure occur in whole or in part.

The computer may be a general-purpose computer, a special-purpose computer, a computer network or other programmable devices. The computer instructions may be stored in or transmitted through a computer readable storage media. The computer readable storage medium may be any available medium that the computer can access or contains a server, a data center and other data storage devices integrated by one or more available media. The available medium may be a magnetic medium or a semiconductor medium, etc.

Embodiment 5

A device for efficiently extracting adaptively selected contactless multi-player heart rates, wherein the device could be applied to the field of sports including volleyball, basketball, soccer, rugby, baseball, and ice hockey, and the embodiments of the present disclosure make no limitation to this.

The embodiments of the present application make special description on the models of the devices, make no limitation to the models of other devices as long as such devices could complete the above functions.

Those skilled in the art could understand that the drawings are only the schematic diagram of a preferred embodiment, and the serial numbers of the above embodiments of the present disclosure are only for description, and does not represent advantages and disadvantages of the embodiments.

The above contents are only better embodiments of the present disclosure, and not used to limit the present disclosure. Any modification, equivalent replacement, and improvement made within the spirit and principle of the present disclosure shall fall within the protection scope of the present disclosure.

What is claimed is:

1. A device for efficiently extracting adaptively selected contactless multi-player heart rates applied to volleyball, basketball, soccer, rugby, baseball, and ice hockey on a court comprises:
  cameras that are deployed in a plurality of angles to obtain videos from all angles of the field and cover the court;
  a processor and a memory integrated with a microcontroller,
  a bus to transmit data signals between the memory and the processor,
  wherein the processor is configured to:
  obtain videos to cover a court from a plurality of angles during players training by the cameras;
  remove players with low contributions to training and games in the videos, wherein a movement trajectory of a ball in the videos is marked to obtain a ball position coordinate set $(X, Y)_{Ball}$ and then, a trajectory position of the players appearing in the videos is marked to obtain a player position coordinate set $(X, Y)_{Obj}$; values of average change angles $$\theta = \arctan\left(\frac{|y_2 - y_1|}{|x_2 - x_1|}\right)$$

of the movement trajectory of the ball and the position coordinate set of the players are calculated respectively; if the average change angle is $|\theta_{Ball} - \theta_{Obj}| < \varphi$, wherein $\varphi$ value is adjusted according to needs, and default $\varphi$ value is 0.5° according to an actual measurement of volleyball training, change directions of the movement trajectory of the ball and the position coordinate set of the players are considered to be consistent approximately; and further, average values of position change $$\text{rates}k = \frac{|y_2 - y_1|}{|x_2 - x_1|}$$

of the movement trajectory of the ball and the trajectory position of the players are calculated, respectively; if the average position change rate is $|k_{Ball}-k_{Obj}|<\tau$, wherein $\tau$ value is adjusted according to the needs, and default $\tau$ is 0.5° according to the actual measurement of volleyball training, the position change rates of the movement trajectory of the ball and the trajectory position of the observed players are considered to be consistent approximately, and when the movement trajectory of the ball is consistent with the movement direction and movement change rate of the players, the players are considered to be related to the movement trajectory of the ball, and the players are retained in the videos as valid players, otherwise the players who are not the valid players are removed from the videos;

detect whether the facial ROIs of the valid players contain perfect eye region features, and use the facial ROIs containing the eye region features as best facial ROIs for heart rate extraction; and analyze the detected best facial ROIs by using blind source separation, and estimate a RGB signal by a JADE algorithm to obtain the heart rate values of the valid players, verifying whether each ROI contains the perfect eye region features, wherein the binocular eyeballs with closed contour are contained, if not, considering that the videos in this angle is invalid, and continuing to select the videos from other angles until all ROIs are retrieved to see whether they contain the perfect eye region features; and calculating the average value of the sum of roundness of a plurality of eyeballs in each ROI and selecting an angle video corresponding to a maximum average value as a best angle video for the heart rate extraction, when detecting a plurality of video angles that contain the perfect eye features;

wherein after obtaining the videos of the valid players in the best facial ROIs that contain the perfect eye region features and the maximum average value of roundness of the eyeballs, a blind source separation (BSS) method is used to extract the heart rates, and the JADE algorithm is used to estimate the heart rates from the RGB images of the best facial ROIs, thus realizing efficiently analyzing and calculating the videos and extracting heart rates with high accuracy;

wherein the processor is further configured to:

make a first judgement to judge whether a movement trajectory of a ball is consistent with a movement direction of an observed player; and make a second judgement to judge whether the movement trajectory of the ball is consistent with a movement change rate of the observed player;

if the two judgments are consistent, the observed player is regarded as the valid players, otherwise the observed player is removed from the videos;

wherein the processor is further configured to:

have a first mark to mark the movement trajectory of the ball in a video clip to obtain a ball position coordinate set;

have a second mark to mark the trajectory position of the observed player appearing in the video clip to obtain the player position coordinate set; and a first calculation to calculate values of the average change angles of the ball position coordinate set and the player position coordinate set respectively by using the obtained ball position coordinate set and the player position coordinate set; if the average change angles of the ball position coordinate set and the player position coordinate set are less than a first threshold, the change directions of the two are considered to be consistent wherein the processor is further configured to comprises:

have a second calculation to calculate average values of position change rates of the movement trajectory of the ball and the trajectory position of the observed player, if the average position change rate is less than a second threshold, the position change rates of the movement trajectory of the ball and the trajectory position of the observed player are considered to be consistent; and wherein the processor is further configured to:

detect whether the facial ROIs of the valid players contain binocular eyeballs with closed contour;

calculate the average value of the sum of roundness of the eyeballs when the binocular eyeballs with closed contour are contained; and when detecting a plurality of video angles that contain the perfect eye features, calculate the average value of the sum of roundness of a plurality of eyeballs in each ROI and select the angle video corresponding to the maximum average value as the best angle video; and when the facial ROIs of the valid players do not contain binocular eyeballs with closed contour, the video from the current angle is considered invalid, and videos continue to be selected from other angles until all ROIs are retrieved to see whether they contain the perfect eye region features, which ensures that all ROIs are traversed and improves the detection accuracy; and output all the ROIs that are retrieved to contain the perfect eye region features.

2. The device for efficiently extracting adaptively selected contactless multi-player heart rates according to claim 1, wherein the multi-angle video acquired by the processor is used for replay after training and games.

3. The device for efficiently extracting adaptively selected contactless multi-player heart rates according to claim 1, wherein the device is applied to volleyball, basketball, soccer, rugby, baseball, and ice hockey.

4. A non-transitory computer readable storage medium, wherein the computer readable storage medium stores a computer program, and the computer program includes program instructions that cause the processor to perform the steps of the device according to the claim 1 when the program instructions are executed by the processor.

5. The device for efficiently extracting adaptively selected contactless multi-player heart rates according to claim 1, wherein the device is applied to volleyball, basketball, soccer, rugby, baseball, and ice hockey.

* * * * *